United States Patent [19]

Schlotzer et al.

[11] Patent Number: 5,589,508

[45] Date of Patent: Dec. 31, 1996

[54] USE OF AN EMULSION TO PREPARE AN INTRAVENSOUSLY ADMINISTERED MEDICAMENT FOR TREATING SKIN DISEASES

[75] Inventors: Ewald Schlotzer, Oberursel; Peter Mayser, Biebertal; Friedrich Grimminger, Butzbach; Werner Seeger, Lahnau; Burghard Weidler; Klaus Sommermeyer, both of Rosbach; Martin Thomas, Frankfurt am Main, all of Germany

[73] Assignee: Fresenius AG, Germany

[21] Appl. No.: 211,644

[22] PCT Filed: Oct. 2, 1992

[86] PCT No.: PCT/EP92/02285

§ 371 Date: Apr. 20, 1994

§ 102(e) Date: Apr. 20, 1994

[87] PCT Pub. No.: WO93/06812

PCT Pub. Date: Apr. 15, 1993

[30] Foreign Application Priority Data

Oct. 11, 1991 [DE] Germany ............... 41 33 694.1

[51] Int. Cl.⁶ ................................................ A61K 31/20
[52] U.S. Cl. ............................................................. 514/560
[58] Field of Search ............................................. 514/560

[56] References Cited

U.S. PATENT DOCUMENTS

| 4,678,808 | 7/1987 | Ward et al. ............................ | 514/560 |
| 5,352,700 | 10/1994 | Frithz et al. .......................... | 514/560 |
| 5,434,183 | 7/1995 | Larsson-Backström ................ | 514/549 |

FOREIGN PATENT DOCUMENTS

| 3722540 | 6/1990 | Germany. |
| WO9008544 | 8/1990 | WIPO. |

OTHER PUBLICATIONS

Burczyk, A., "Bedeutung ungesättigter Fettsäuren in Nahrung und Kosmetik," *Seifen–Öle–Fette–Wachse* 115:462–463 (1989). (Summary Only).

Chapkin, R. S. et al., "Dietary Influences of Evening Primrose and Fish Oil on the Skin of Essential Fatty Acid–Deficient Guinea Pigs," *J. Nutrition* 117:1360–1370 (Aug. 1987).

Horrobin, D. F., "Low Prevalances of Coronary Heart Disease (CHD), Psoriasis, Asthma and Rheumatoid Arthritis in Eskimos: Are They Caused by . . . ?," *Medical Hypotheses* 22:421–428 (Apr. 1987).

Lowe, N. J. et al., "Linoleic Acid Effects on Epidermal DNA Synthesis and Cutaneous Prostaglandin Levels in Essential Fatty Acid Deficiency," *J. Invest. Dermatol.* 70:200–203 (Apr. 1978).

Martinez, M. and Ballabriga, A., "Effects of Parenteral Nutrition with High Doses of Linoleate on the Developing Human Liver and Brain," *Lipids* 22:133–138 (1987).

Simopoulos, A. P., "Summary of the NATO Advanced Research Workshop on Dietary ω3 and ω6 Fatty Acids: Biological Effects and Nutritional Essentially," *J. Nutrition* 119:521–528 (Apr. 1989).

Ziboh, V. A. et al., "Effects of Dietary Supplementation of Fish Oil on Neutrophil and Epidermal Fatty Acids", *Arch. Dermatol.* 122:1277–1282 (Nov. 1986).

*Primary Examiner*—Gary Geist
*Assistant Examiner*—Barbara S. Frazier
*Attorney, Agent, or Firm*—Sterne, Kessler, Goldstein & Fox P.L.L.C.

[57] ABSTRACT

An emulsion containing one or several polyunsaturated, long-chain omega-3 and/or omega-6 fatty acids or their pharmaceutically tolerable esters or salts, as well as usual adjuvants and additives, is used to produce an intravenously administered medicament for treating skin diseases, in particular inflammatory skin diseases, as well as diseases of the dermatitis or eczema group. Preferably, fatty acids containing 18–22 carbon atoms, as well as their pharmaceutically tolerable esters of salts, are used. These acids or their pharmaceutically tolerable esters or salts may be used in their pure form or as components of oils, such as fish oil, highly-purified fish oil concentrates, linseed oil, primrose oil, borage oil or soya oil. Specially preferred are the pharmaceutically tolerable esters or salts of said acids, in particular the pharmaceutically tolerable esters, especially those derived from eicosapentaenic acid. The emulsions may be further intravenously administered in the framework of a combined therapy with presently known therapies of skin diseases.

13 Claims, 5 Drawing Sheets

USE OF AN EMULSION TO PREPARE AN INTRAVENSOUSLY ADMINISTERED MEDICAMENT FOR TREATING SKIN DISEASES

This application is a 371 of PCT/EP92/02285, filed Oct. 2, 1992.

TECHNICAL FIELD

The invention concerns the use of an emulsion that contains one or more, polyunsaturated, long-chain omega-3 fatty acids and/or omega-6 fatty acids or their pharmaceutically tolerable esters or salts for, respectively, the intravenous administration for the treatment of skin diseases, or to prepare an intravenously administered medicament for treating skin diseases, particularly inflammatory skin diseases, as well as diseases of the dermatitis and eczema family, in particular of skin diseases of the dermatitis and eczema family.

Today, skin diseases represent a high percentage of diseases in humans and animals with, for example, psoriasis are among the most common skin diseases, from which approximately 1 to 2% of the population suffers.

STATE OF THE ART

The necessity of essential fatty acids for the structure and function of the skin is known. Using animal models, rats have who were given a diet free of these fatty acids have exhibited developmental impairments and skin alterations with reddening, dandruff, and hyperkeratoses in the region of the sebaceous glands. Other alterations included increased effluvium, hyperproliferation with increased epidermal cell turn-over, impaired healing of wounds, and increased transepidermal water loss. These skin alterations were reversible upon substitution. The principal sources of the essential fatty acids, which are classified by the position of their first double bond as either omega-3 or omega-6 fatty acids, are, primarily, cold-water fish (for omega-3 fatty acids) or vegetable oils (for omega-6 fatty acids). In mammals, the presence of different enzymes which give unsaturation and enzymes which give elongation can lead to the formation of additional secondary products.

The observation that populations that exhibit a high level of omega-3 fatty acid consumption (for example, Eskimos) exhibit only one-twentieth the incidence of psoriasis of comparable populations who nourish themselves primarily with omega-6 fatty acids, has led to several clinical studies which examined the effect of a diet rich in fish oil, that is, an oral application of fish oil, on the course of various forms of psoriasis (for example, *The Lancet*, Feb. 20, 1988, page 378; *Journal of the American Academy of Dermatology*, 1988, volume 18, pages 1267 through 1273; *British Journal of Dermatology*, 1987, 117, pages 599–613).

While the indications are not uniform for chronic, constant, common psoriasis, they do, however, agree on the fact that a clinical improvement results from a linear dosage/effect relationship. For the exudative forms (exanthematous psoriasis, pustular psoriasis), but also for psoriatic arthritis, the trend appears to be toward uniformly positive indications, although the published number of cases is still small. This therapeutic reasoning is based on the suppression and antagonization of the metabolism of arachidonic acid vital to the pathogenesis by inclusion of the structurally-related eicosapentaenoic acid (EPA) in the lipid metabolism of both keratinocytes as well as neutrophile granulocytes. Granulocytes seem to play an important role, particularly in inflammatory forms of psoriasis, a fact that is supported by increased function parameters as well as the histological characteristics of the infiltration of the epidermis and the formation of so-called Munroe's micro-abscesses. In particular in pustular forms, the increased chemotactic and pro-inflammatory activity results in the formation of clinically visible pustules on skin altered by inflammation.

As a potent chemotactic substance, LTB4, a lipoxygenase product of the arachidonic acid that has been found in increased levels in psoriatic lesions, can explain these findings. In addition, it stimulates keratinocyte proliferation in cell cultures.

The oral ingestion of eicosapentaenoic acid (omega-3 fatty acid) contained in fish oil, the metabolism of the arachidonic acid (omega-6 fatty acid) can be competatively inhibited to such an extent that biologically less potent metabolites are produced: in the case of LTB4, for example, the significantly less chemotacticly effective LTB5. This is explained by the uptake of eicosapentaenoic acid in place of arachidonic acid in the cell membrane, and by the competition of this substance for the enzymes, cyclooxygenase and lipoxygenase. The studies carried out showed that the oral treatment of skin diseases with fish oil (for example, in the form of the oral administration of fish oil capsules) requires a long treatment period (up to several months), during the course of which in some cases very large amounts (for example, 10 to 75 g) of fish oil must be taken daily, whereby correspondingly severe gastrointestinal complaints (for example, nausea, a feeling of fullness, retching, eruction) arise during the course of the treatment. A further aspect of this type of oral fish oil therapy is the poor patient compliance.

Other forms of treatment of skin diseases, including severe psoriasis, include the treatment with retinoids such as eretinate and acitretin. Significant disadvantages of this treatment are hyperlipidemia, including hypertriglyceridemia, hypercholesteremia and a reduced level of high-density lipoprotein cholesterol (HDL-C). For oral therapy lasting for a longer period of time, the side-effects induced by retinoid treatment represent a potent risk for severe cardiovascular illnesses. Other presently known treatment methods for skin diseases are treatment with cignolin, non-steroid antiphlogistics, antihistamines, or corticosteroids, as well as photo or balneophototherapy. But this treatment methods also lead to considerable side-effects, whereby burns occur as the most common side-effect for treatment with cignolin and for photo or balneophototherapy, while for treatment with corticosteroids, skin atrophy has been observed. What all these standard treatments, with the exception of corticosteroid therapy, have in common however, is the disadvantage that they require a relatively long treatment period. Corticosteroids act very rapidly, however, because they lead to skin atrophy, they can only be used for a short period. Treatment with non-steroid antiphlogistics or with antihistamines are, in addition, only alleviating measures, whose side-effects lead to stomach complaints or induce fatigue.

DESCRIPTION OF THE INVENTION

The object of the invention is thus a suitable agent and process for the treatment of skin diseases, particularly inflammatory skin diseases, as well as diseases of the dermatitis and eczema family, in particular of skin diseases of the dermatitis and eczema family, that does not display the disadvantages of the known agents and processes, and with whose aid visible treatment successes can be achieved within a shorter treatment period.

In accordance with the invention, it was surprisingly found that, by the intravenous administration of fat emulsions containing one or more polyunsaturated, long-chain omega-3 fatty acids and/or omega-6 fatty acids or their pharmaceutically tolerable esters or salts for the treatment of skin diseases, particularly inflammatory skin diseases, as well as diseases of the dermatitis and eczema family, in particular of skin diseases of the dermatitis and eczema family, after only a few days of treatment a therapeutic success is already visible, and the disadvantages or side-effects associated to the known standard treatments can be avoided.

Aside from the rapid onset of the effect with intravenous treatment, other advantages over previous standard treatment methods lie in the improved patient compliance—that is, the more ready acceptance of the treatment on the part of the patients—reduced strain for the patients due to the intravenous treatment, no appearance of gastrointestinal problems, as well as a shorter hospital stay for inpatients, a shorter treatment period, and therefore a reduction in the treatment costs. While the oral treatment of the skin diseases described above requires several weeks (at least 6 weeks) up to several months with the daily administration of 20 or more fish oil capsules, the intravenous treatment in accordance with the invention with the emulsion requires only a few days of treatment with a daily infusion period of approximately one hour.

Preferred are emulsions for use in accordance with the invention with polyunsaturated, long-chain, omega-3 and/or omega-6 fatty acids containing 18 to 22 C atoms, as well as their esters and salts. Examples of suitable omega-3 fatty acids are α-linolenic acid, eicosapentaenoic acid (EPA), and docosahexaenoic acid (DCHA), whereby preferably EPA and DCHA, particularly EPA, is used. One or more of the omega-3 fatty acids can be present in the emulsions. The acids or their pharmaceutically tolerable esters or salts can be used either in their pure form, or as a component of fish oil, highly purified fish oil concentrates or linseed oil, preferably as fish oil or highly purified fish oil concentrations. Suitable fish oils are, for example, those types which are technically recovered in substantial quantities from cold-water fish. Examples of such fish oils include pilchard oil, menhaden oil, Peruvian fish oil, sardine oil, salmon oil, herring oil, and mackerel oil. Preferred are highly purified fish oil concentrations such as are produced from mackerel, sardines, herrings, or salmon, Whereby these have an EPA content of 20 to 40%, preferably at least 26% (based on the fatty acid methyl ester of the fish oil concentrate). Examples of suitable fish oil emulsions are described in DE PS 37 22 540, to which the reader is referred.

Examples of suitable omega-6 fatty acids include linoleic acid, γ-linolenic acid, dihomo-γ-linolenic acid, and arachidonic acid, whereby γ-linolenic acid and dihomo-γ-linolenic acid are preferred. The emulsion applied in accordance with the invention can contain one or more omega-6 fatty acids. Omega-6 fatty acids or their pharmaceutically tolerable esters or salts can be used in either their pure form or in the form of components of oils, for example, primrose oil, borage oil, or soybean oil. Preferably primrose oil is used.

The pharmaceutically tolerable esters and salts of the cited omega-3 and/or omega-6 fatty acids are preferably used, whereby the pharmaceutically tolerable esters of these acids are particularly preferred. Pharmaceutically tolerable esters of the omega-3 and omega-6 fatty acids include the ethyl esters or glycerin esters, for example, mono-, di-, or triglycride esters, whereby triglycerides are preferred. Sodium salts are suitable as pharmaceutically tolerable salts.

The emulsions employed in accordance with the invention can contain either:

a) Omega-3 fatty acids, their pharmaceutically tolerable esters or salts in pure form or as a component of oils as were cited above, or;

b) Omega-6 fatty acids, their pharmaceutically tolerable esters or salts in pure form or as a component of oils as were cited above, or;

c) A mixture of the acids cited in a) and in b) above, or their pharmaceutically tolerable esters or salts.

For example, in the emulsions employed in accordance with the invention can contain a mixture of fish oil and other oils such as primrose oil, borage oil, or soybean oil, whereby the ratio of fish oil to the other oils (by weight) is most suitably in the range between 9:1 and 1:9. For example, the ratio of fish oil to primrose oil and/or borage oil can be 1:1, and the ratio of fish oil to soybean oil can be 7:1.

The omega-3 fatty acids and/or omega-6 fatty acids or their pharmaceutically tolerable ester or salts are present in quantities of 5 to 45% by weight, preferably in quantities of 10 to 30% by weight and, in particular, in quantities of 10–20% by weight in the emulsions employed in accordance with the invention.

Preferred in accordance with the invention are those emulsions based solely on omega-3 fatty acids, their esters or salts in pure form or in the form of components of oils, such as were cited above, in particular, those based on fish oils.

The emulsions employed in accordance with the invention also contain at least one, physiologically safe emulsifier. Suitable are phospholipids with an animal or vegetable origin, preferably those phospholipids which contain EPA as a polyunsaturated fatty acid. Ovolecithin is particularly suitable.

The emulsifier is present in the emulsion in quantities of 5 to 15% by weight (based on the fat content), preferably in quantities of 5 to 12% by weight (based on the fat content).

In addition, vitamin E, for example in the form of tocopherol or pharmaceutically safe tocopherol ester, for example, tocopherol acetate, can also be present in the emulsion in quantities of 0.15 to 1.5% by weight (based on the fat content), to act as an antioxidant.

As additional additives, the emulsion employed in accordance with the invention can also contain such as the common aids as conventional emulsion stabilizers, isotonic additives and/or co-emulsifiers as well as selenium compounds, if required. A suitable selenium compound is, for example, $Na_2SeO_3 \times 0.5H_2O$.

Suitable isotonic additives include the commonly employed isotonic agents such as glycerin, glucose, xylose, and sorbite, whereby glycerin is preferred.

A suitable, preferable emulsion employed in accordance with the invention has, for example, the following composition:

| | |
|---|---|
| Fish oil | 100 mg/ml |
| Glycerin (isotonic agent) | 25 mg/ml |
| Ovolechitin | 12 mg/ml |
| Vitamin E | 0.15 mg/ml |
| Water (for injection) to make 1 ml. | |

The fish oil used in the above-cited composition is preferably highly refined fish oil that has been enriched in omega-3 fatty acids in triglyceride compounds by means of a specific procedure as is described in DE PS 37 22 540. It contains at least 40% by weight omega-3 fatty acids. The total EPA and DCHA content of the fish oil as triglyceride components lies in the range of 25 to 50% by weight, preferably in the range of 35 to 50% by weight (each value determined on the basis of the surface percentage in a gas chromatogram). In the fish oil, the EPA and DCHA can be present in varying quantitative ratios, that can be determined by measuring the respective surfaces in the gas chromatogram. The quantitative ratios depend on the nature of the fish oil used, and on the degree of enrichment of omega-3 fatty acids achieved. Fish oils in which EPA and DCHA as triglyceride components are present in a quantitative ratio of EPA to DCHA in the range between 0.5 to 2.6 (surface ratio in the gas chromatogram), are the fat emulsions whose use is preferred.

The fat emulsions employed in accordance with the invention are oil-in-water emulsions (O/W) for which the external phase consists of distilled water, suitable for intravenous administration.

The emulsions employed in accordance with the invention are produced in the conventional manner. A suitable process is described, for example, in DE PS 37 22 540.

In accordance with the invention, the emulsions can be employed for the intravenous administration for the treatment of skin diseases such as:

1. Skin diseases that are induced or maintained by derivatives of arachidonic acid formed by granulocytes or their sub-populations (neutrophils, eosinophils), by keratinocytes or by both, whereby in particular, the following are to be mentioned:

a) Inflammatory skin diseases such as common psoriasis, pustular psoriasis, psoriatic arthritis, allergic vasculitis;

b) Diseases of the dermatitis and eczema family such as constitutional neurodermatitis, contact dermatitis (allergic/toxic);

c) Inflammatory skin diseases with eosinophilia (hypereosinophilia syndrome, eosinophilic cellulitis, hypereosinophilic dermatitis);

d) Vesiculated dermatoses such as common pemphigus, vesiculated pemphigoid;

e) Photodermatoses, i.e. acute photodermatitis, polymorphous photodermatoses.

2. Skin diseases in conjunction with impaired function of the immune system, in particular with over-stimulated immune function, whereby the following are particularly to be named: lupus erythematosus and other, so-called collagenoses, areal alopecia, graft versus host disease, pilaris.

The emulsions are intravenously employed in accordance with the invention, particularly in the treatment of inflammatory skin diseases as well as diseases of the dermatitis and eczema family, in particular for the treatment of diseases of the dermatitis and eczema family. In accordance with the invention, it was surprisingly discovered that, with intravenous administration of fat emulsions, aside from achieving higher effectiveness levels, acute anti-inflammatory effects can also be achieved. In accordance with the existing view, the effect of the omega-3 fatty acids, in particular the effect of the EPA, is based on an inclusion of these fatty acids in place of arachidonic acid in the cell membrane, from which they are released upon appropriate stimuli by phospholipases and, depending on the enzymatic composition of the cell in question, are transformed into corresponding mediators with cyclo- and/or lipoxygenases. However, with this concept, effects can only be achieved after a multiple-week therapy period, because eicosapentaenoic acid is only obtained over a complex, indirect path via a modulation of the cellular phospholipid composition. In accordance with the invention, it was surprisingly discovered that, with respect to the therapeutic employment in diseases effecting the cutaneous system, an intravenous application of a fish oil emulsion allows an acute therapeutic intervention in the previously cited diseases. This may possibly be the result of the fact that, in an inflammatory focus, free EPA is also absorbed directly by cells capable of eicosanoid synthesis in competition to free extracellular arachidonic acid, and can be metabolized by them. Therefore, the acute, anti-inflammatory, therapeutic intervention is a new possibility in the treatment of the diseases cited above.

With respect to the diseases listed, acute immunodulatory effects result via the alteration of the mediator profile (cyclo- and lipoxygenase products), as well as the composition of the cell membrane, because the fluidity and therefore the possibility for antigen presentation at the cell membrane changes with the composition of its lipid portion. Further, with the substitution of omega-3 fatty acids, the properties of lymphocytes (i.e. suppression of killer cells) and macrophages (reduced eicosapentaenoic acid production with unaltered phagocytic capability and production of oxygen radicals) are altered.

The intravenous administration of the emulsion in cases of skin diseases in accordance with the invention can, in addition, take place within the framework of a combination therapy, in particular in combination with a therapy with:

a) retinoids, systemic;

b) cignolin, externally;

c) phototherapy (SUP, PUVA) or balncophototherapy;

d) corticosteroids (internal/external)

e) non-steroidal antiphlogistics, and/or;

f) antihistamines.

Thus, when retinoids are used in cases of psoriasis and other inflammatory skin diseases, the additional intravenous administration of omega-3 fatty acids leads, aside from the additional, anti-inflammatory effect, to the observation of a rapid drop in the retinoid-induced serum lipid increase. In the combination therapy with the intravenous administration of the emulsions and photo or cignolin therapy, the erythema threshold can be raised so that the dosage of conventional therapeutic agents can be more rapidly increased, or their undesirable side-effects can be lessened. In the combination therapy of intravenous administration of the emulsions and the conventional treatment with corticosteroids, the usually required dosage of corticosteroids is reduced and, consequently, the skin atrophy produced by them is lessened. The combination of the intravenous administration of the emulsions with non-steroidal antiphlogistics or antihistamines correspondingly permits the reduction of the conventionally required dosage and time period of administration of the agents, and therefore also a reduction of the disadvantages normally associated with their use.

For the intravenous administration in the treatment of skin diseases, an amount of fat emulsions that corresponds to 0.01 to 0.3 g, preferably 0.05 to 0.15 g of the cited fatty acid(s), their esters or salts, per kg of body weight per day, is suitable. Thus, for example, an amount of fat emulsion can be employed as corresponds to 0.01 to 0.2 g, preferably 0.05 to 0.1 g of EPA, its esters or salts, per kg of body weight per day, or which corresponds to 0.05 to 0.5 g of oil (for example, fish oil and/or primrose oil), per kg of body weight per day, preferably 0.1 to 0.5 g, in particular, 0.1 to 0.3 g of fish oil per kg of body weight per day, can be employed.

The fat emulsions in accordance with the invention are not toxic.

METHODS OF REALIZING THE INVENTION

Figure 1A:
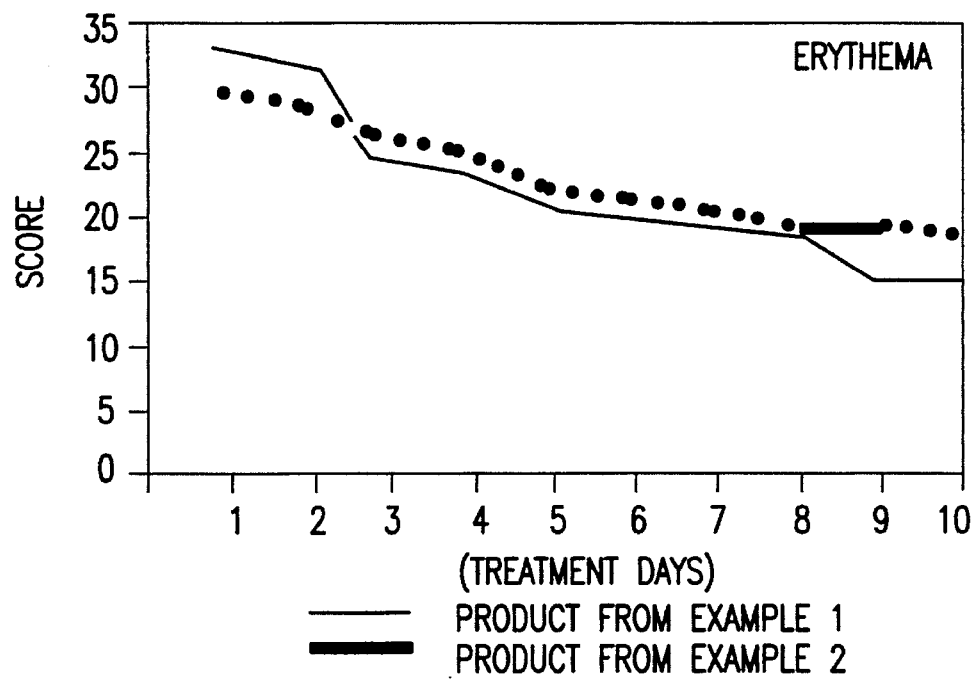
FIGS. 1a–1b show graphs depicting the mean score values (FIG. 1a) and relative scores (FIG. 1b) for erythema improvement from example 1 ("T") and example 2 ("K"), as listed under "1. Erythema" herein.

The following examples serve to further clarify the invention presented here.

EXAMPLE 1

A fat emulsion suitable for intravenous administration was produced from the components listed below:

| | |
|---|---|
| Fish oil | 100 mg |
| Glycerin | 25 mg |
| Ovolecithin | 12 mg |
| Vitamin E | 0.15 mg |
| Water (for injection) to make 1 ml. | |

The fish oil used is highly-refined and contains at least 40% by weight of omega-3 fatty acids and was produced in the manner described in example 1 of DE PS 37 22 540.

The fat emulsion was produced in the same manner as described in example 5 of DE PS 37 22 540.

The toxicological study of the 10% fish oil emulsion produced above, using two species—beagles and Charle's River rats—carried out over 4 weeks showed that these fish oil emulsions displayed no indications of any kind of systemic toxicity or intravascular irritation after intravenous administration of doses up to 5,000 mg/kg of body weight per day.

EXAMPLE 2

A 10% fat emulsion suitable for intravenous administration was produced from the components listed below:

| | |
|---|---|
| Soybean oil | 100 mg |
| Glycerin | 25 mg |
| Ovolecithin | 12 mg |
| Water (for injection) to make | 1 ml. |

The fat emulsions produced in example 1 and 2 were examined in the following manner with respect to their effectiveness when intravenously administered for skin diseases:

Ten patients suffering from acute, exanthematous psoriasis were included in the study, whereby the clinical examination of the emulsion in accordance with example 1 was studied with six patients, while four patients received the emulsion in accordance with example 2. The individual patient data are summarized in table 1.

The study was carried out under double-blind conditions. Twice per day at intervals of 12 hours over a period of 10 days, the patients were intravenously given 50 ml of the respective fat emulsion (emulsion from example 1 or 2). The patients were examined daily with regard to the alteration in the clinical picture and, at certain intervals and using conventional methods, with regard to the changes in the EPA metabolites, the triglyceride content, the cholesterol content, and the IgE. The determination of the EPA metabolites was carried out with the aid of high-performance liquid chromatography (HPLC), using both the reverse as well as the straight-line method. Triglycerides and cholesterol were determined with the aid of enzymatic chromatometry (GPO-PAP method and CHOD-PAP method respectively). The following criteria were employed in the evaluation of the clinical picture:

Erythema, scaling, exudation, subjective improvement, and improvement in itching.

The individual results gathered in the study are as follows, expressed as mean score values:

| Mean score values (A1–A10) | | | | | |
|---|---|---|---|---|---|
| 1. Erythema | | | | | |
| Day | 1 | 2 | 3 | 4 | 5 |
| T (6) | 32.6 | 31.8 | 26 | 25.8 | 23.5 |
| K (4) | 29 | 28.5 | 26.75 | 26.5 | 24.5 |
| Day | 6 | 7 | 8 | 9 | 10 |
| T (6) | 22.5 | 21.3 | 19.8 | 17.3 | 16.8 |
| K (4) | 24 | 22.75 | 22 | 21.75 | 20.5 |
| Relative score (%) | | | | | |
| Day | 1 | | | | Day 10 |
| T (6) | 100 | | | | 51.5 |
| K (4) | 100 | | | | 70.7 |
| 2. Scaling | | | | | |
| Day | 1 | 2 | 3 | 4 | 5 |
| T (6) | 29 | 27.3 | 24.5 | 23.5 | 20.3 |
| K (4) | 20.5 | 18.25 | 16.75 | 16.75 | 16.25 |
| Day | 6 | 7 | 8 | 9 | 10 |
| T (6) | 20.1 | 18 | 16.8 | 15.5 | 15.2 |
| K (4) | 16.25 | 15.5 | 15.25 | 15.25 | 15.25 |
| Relative score (%) | | | | | |
| Day | 1 | | | | Day 10 |
| T (6) | 100 | | | | 52.4 |
| K (4) | 100 | | | | 74.4 |
| 3. Exudation | | | | | |
| Day | 1 | 2 | 3 | 4 | 5 |
| T (6) | 32.4 | 31.4 | 28.4 | 27.8 | 26 |
| K (4) | 9.25 | 9.75 | 9.75 | 9.75 | 9.75 |

-continued

Mean score values (A1–A10)

| Day | 6 | 7 | 8 | 9 | 10 |
|---|---|---|---|---|---|
| T (6) | 25.2 | 22.4 | 21.4 | 18.8 | 17.6 |
| K (4) | 9.75 | 9.75 | 9.75 | 9.75 | 9.75 |

Relative score (%)

| Day | 1 | Day 10 |
|---|---|---|
| T (6) | 100 | 54.3 |
| K (4) | 100 | 105 |

Note: No exudative component could be determined for one of the patients who was treated with the emulsion from example 1, as well as for two of the group who were treated with the emulsion from example 2.

T=Emulsion from example 1.
K=Emulsion from example 2.

4. Subjective improvement

| Day | 1 | 2 | 3 | 4 | 5 |
|---|---|---|---|---|---|
| T (6) | 18.8 | 18 | 22 | 23.5 | 23.3 |
| K (4) | 23.25 | 24.25 | 23 | 23.75 | 23.25 |

| Day | 6 | 7 | 8 | 9 | 10 |
|---|---|---|---|---|---|
| T (6) | 24.1 | 24.8 | 27.6 | 28.5 | 28.8 |
| K (4) | 23.5 | 24 | 22.25 | 23.75 | 23.75 |

Relative score (%)

| Day | 1 | Day 10 |
|---|---|---|
| T (6) | 100 | 153 |
| K (4) | 100 | 102 |

5. Improvement in itching

| Day | 1 | 2 | 3 | 4 | 5 |
|---|---|---|---|---|---|
| T (6) | 3.5 | 3 | 4.5 | 5.5 | 5.1 |
| K (4) | 3.5 | 3.5 | 3.25 | 3.75 | 3.75 |

| Day | 6 | 7 | 8 | 9 | 10 |
|---|---|---|---|---|---|
| T (6) | 5.3 | 5.1 | 5.2 | 5 | 5.8 |
| K (4) | 3.75 | 3.75 | 4 | 3.75 | 4 |

Relative score (%)

| Day | 1 | Day 10 |
|---|---|---|
| T (6) | 100 | 167.7 |
| K (4) | 100 | 114 |

Figure 1B:
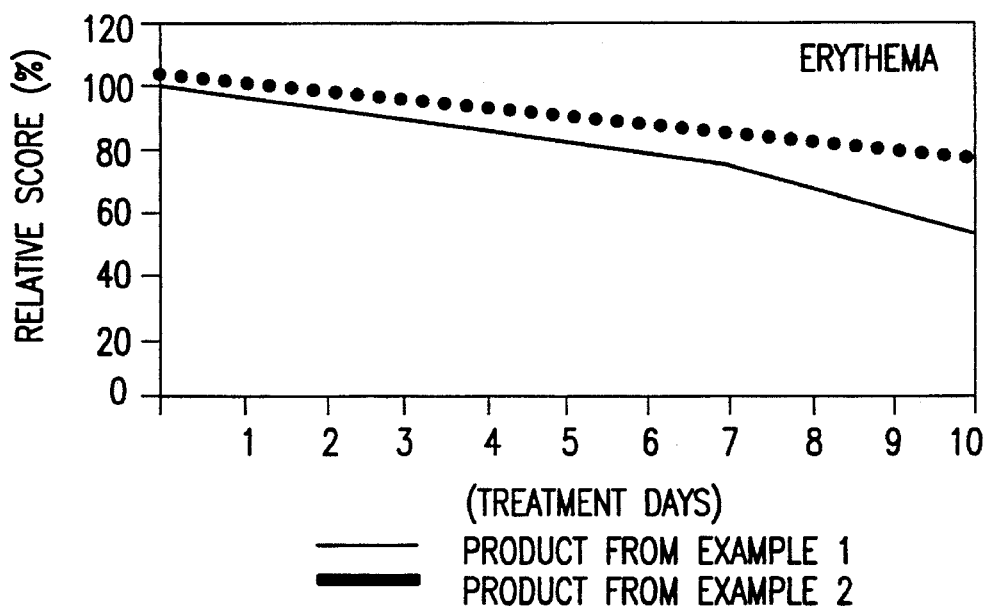
Figure 2A:
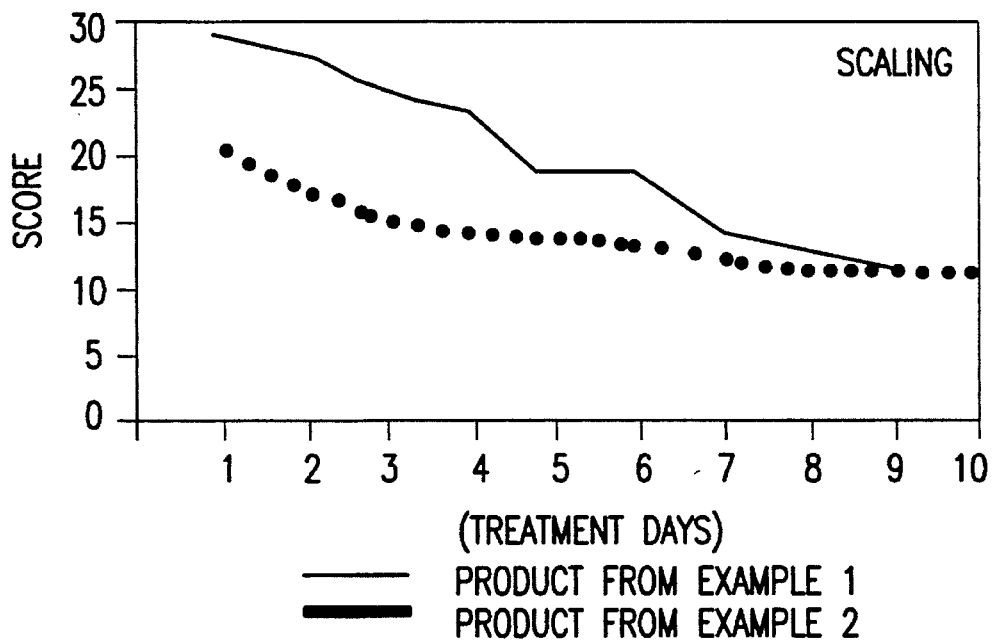
FIGS. 2a–2b show graphs depicting the mean score values (FIG. 2a) and relative scores (FIG. 2b) for scaling improvement from example 1 ("T") and example 2 ("K"), as listed under "2. Scaling" herein.
Figure 2B:
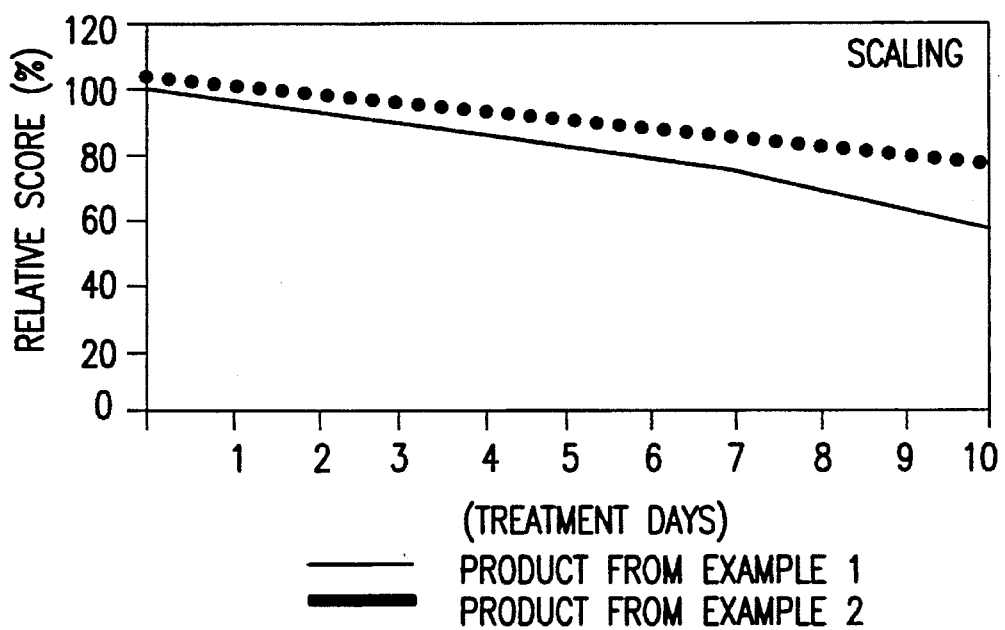
Figure 3A:
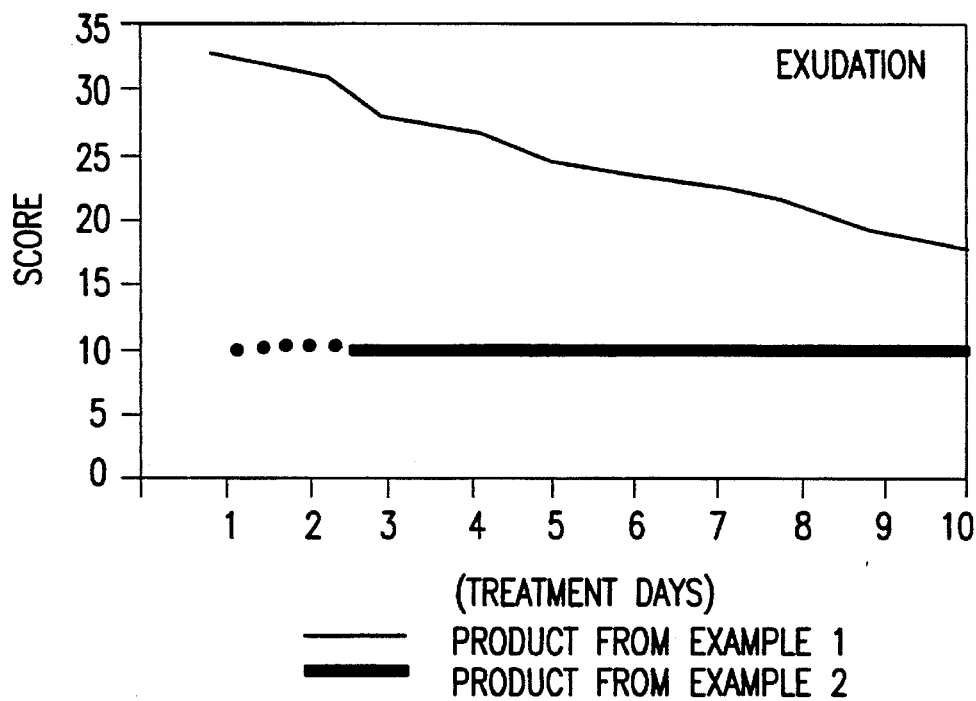
FIGS. 3a–3b show graphs depicting the mean score values (FIG. 3a) and relative scores (FIG. 3b) for exudation improvement from example 1 ("T") and example 2 ("K"), as listed under "3. Exudation" herein.
Figure 3B:
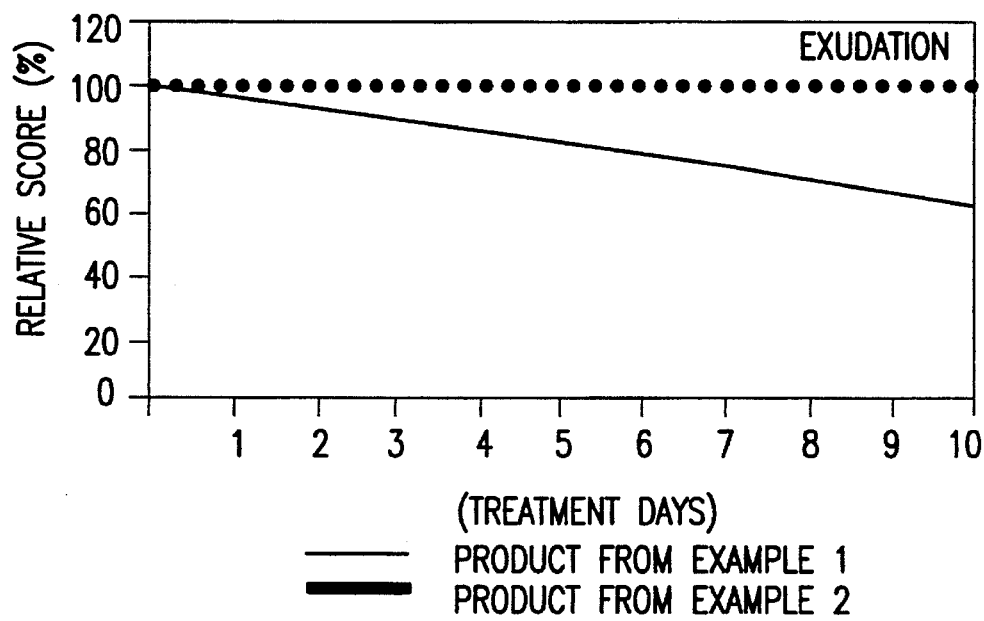
Figure 4A:
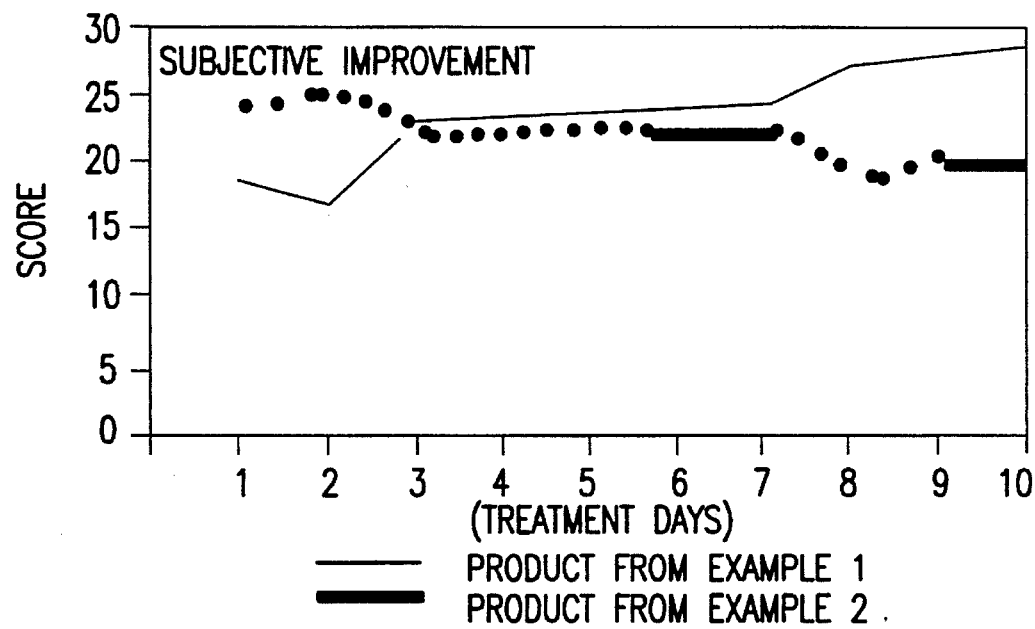
FIGS. 4a–4b show graphs depicting the mean score values (FIG. 4a) and relative scores (FIG. 4b) for subjective improvement from example 1 ("T") and example 2 ("K"), as listed under "4. Subjective improvement" herein.
Figure 4B:
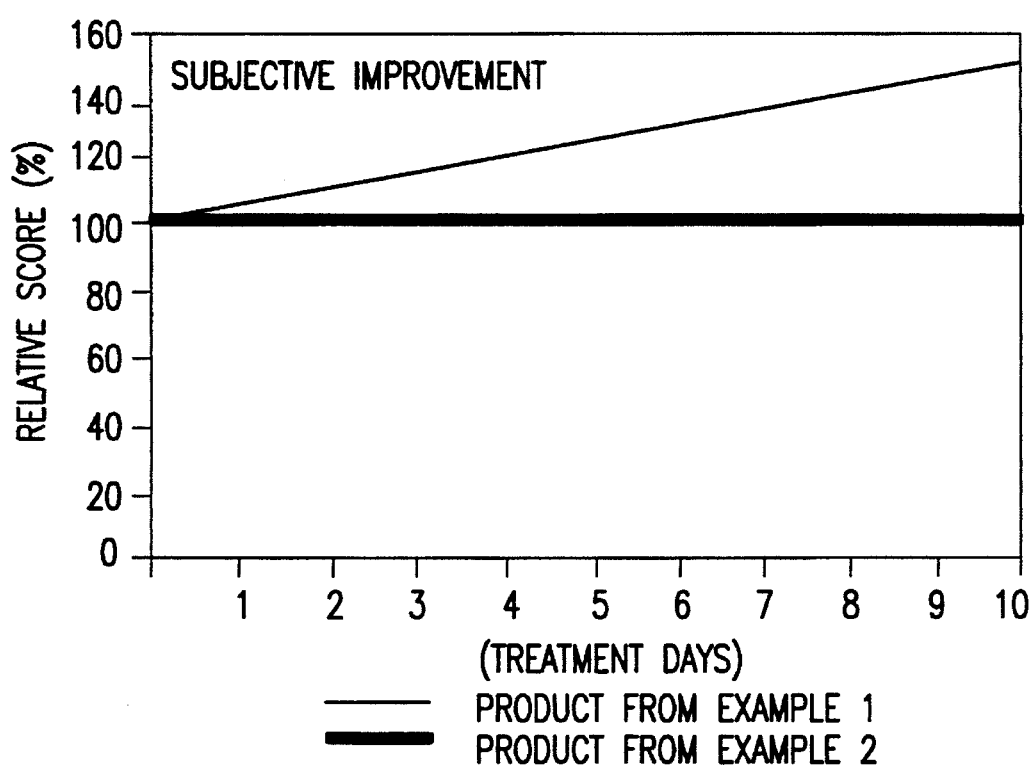
Figure 5A:
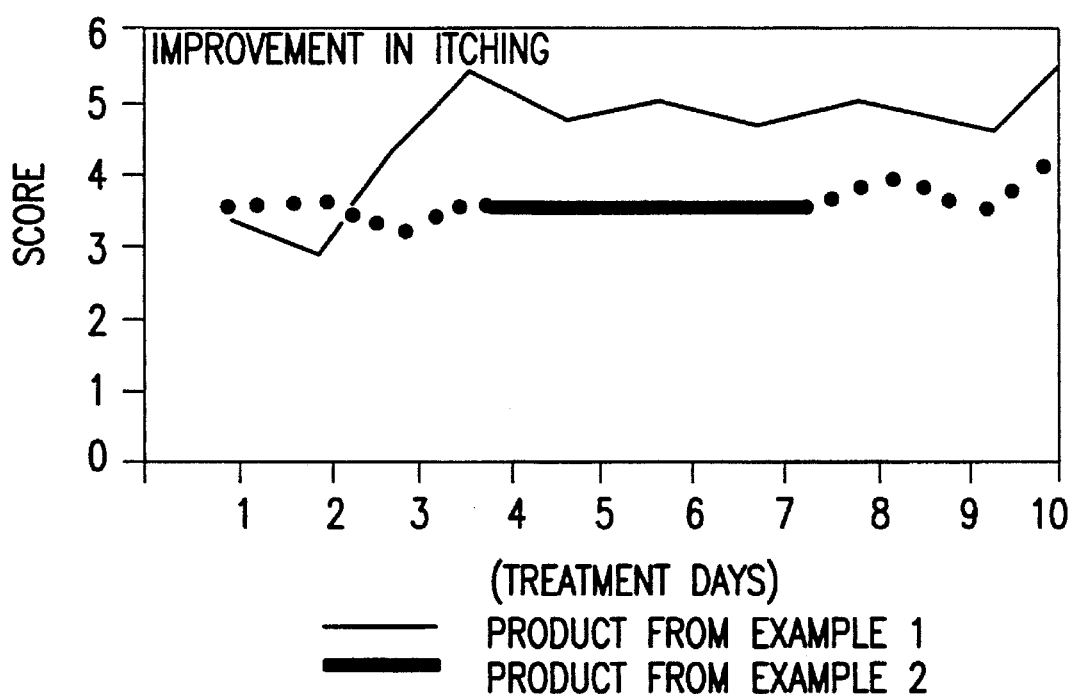
FIGS. 5a–5b show graphs depicting the mean score values (FIG. 5a) and relative scores (FIG. 5b) for improvement in itching from example 1 ("T") and example 2 ("K"), as listed under "5. Improvement in itching" herein.
Figure 5B:
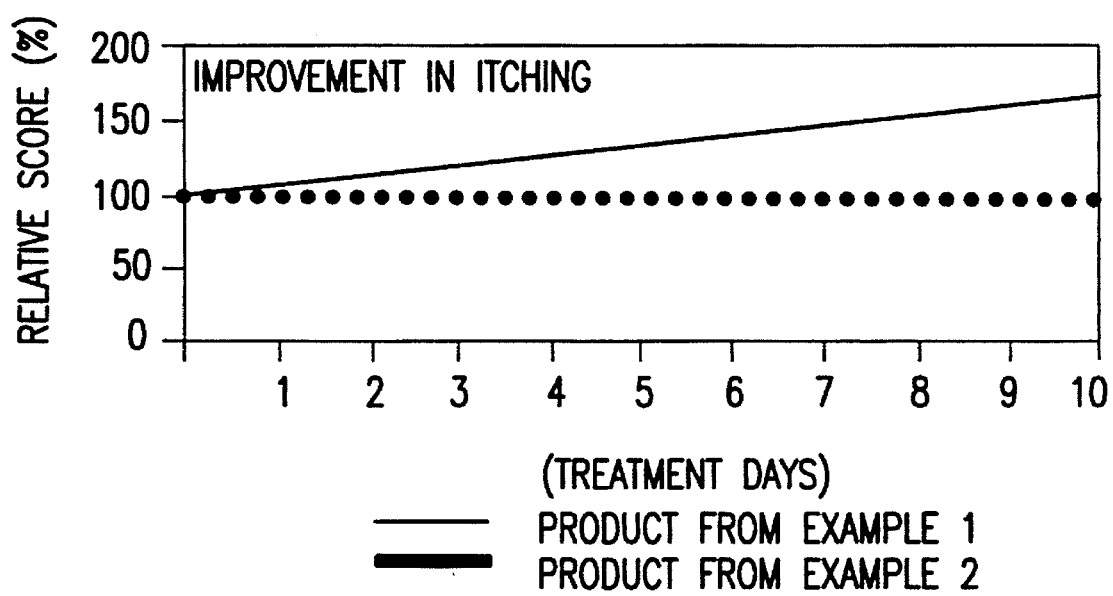

Note:
1. For criteria 1–4, a maximum score value of 50 can be achieved; for criterion 5, a maximum value of 10.
2. Criterion 5 (improvement in itching) is part of criterion 4 (subjective improvement), that is, it is also included in this evaluation.
3. For criteria 1–3, a drop in the score indicates an improvement; for criteria 4 and 5, a deterioration. For clarification, the mean score values for the individual appearance picture of the skin and the subjective feelings respectively, are summarized in FIGS. 1 to 5. In addition, table 2 also shows the values for EPA metabolites, triglyceride content, cholesterol, and IgE determined during the course of the study.

The results achieved in the studies show that, for the intravenous administration of the emulsion in accordance with example 1, a noticeable improvement in the clinical condition occurred within a very few days, while, with the emulsion in accordance with example 2, a mild improvement in the clinical condition took place in all patients after a few days. The improvement in the clinical condition correlates with the increase of the EPA metabolites and, in addition, with the absolute level of the serum IgE value, so that, in particular, a neurodermatitis can be influenced with the intravenous treatment in accordance with the invention. Aside from a mild venous irritation, no side-effects were observed.

EXAMPLE 3

Example 1 was repeated, with the exception that, in place of fish oil, the same amount of primrose oil was employed.

EXAMPLE 4

Example 1 was repeated, with the exception that 50 mg of the fish oil used in example 1 was replaced by 50 mg of primrose oil. In the intravenous administration of the fat emulsions obtained in accordance with this example, similar examination results were obtained to those described above for example 1.

EXAMPLE 5

Example 1 was repeated, with the exception that 1 μg of selenium in the form of $Na_2SeO_3 \times 5H_2O$ was added to the emulsion produced in example 1. The intravenous administration for skin diseases of the emulsion produced in this manner achieved the same results as those described for example 1.

TABLE 1

| No. | Patient | Age | Sex | Weight [kg] | Diagnosis | Spread [%] | Disease duration |
|---|---|---|---|---|---|---|---|
| A1 | HG | 27 | Male | 73 | Acute ex. ps. | 20 | 12 years |
| A2 | EL | 42 | Male | 95 | Acute ex. ps. | 25 | 20 years |
| A3 | MO | 21 | Male | 67 | Acute ex. ps. | 18 | 10 years |
| A4 | ZH | 47 | Male | 118 | Acute ex. ps. | 30 | 20 years |
| A5 | TF | 30 | Male | 72 | Acute ex. ps. | 10 | 20 years |
| A6 | LJ | 65 | Male | 66 | Acute ex. ps. | 10 | 0.5 years |
| A7 | HF | 28 | Male | 71 | Acute ex. ps. | 12 | 15 years |
| A8 | HS | 62 | Male | 95 | Acute ex. ps. | 90 | 31 years |
| A9 | HK | 55 | Male | 88 | Acute ex. ps. | 35 | 36 years |
| A10 | GU | 25 | Female | 65 | Acute ex. ps. | 15 | 2 years |

TABLE 2

| No. | Medication | Score change (d1 = 100%) E | S | EX | [%] SB | J | EPA Metabolites | Triglycerides | Cholesterol | IgE |
|---|---|---|---|---|---|---|---|---|---|---|
| A1 | T | −58 | −56 | −76 | +45 | +50 | +786% | −46% | −3% | 780 |
| A2 | K | −17 | −30 | −11 | +50 | +300 | −26% | +50% | +31% | 161 |
| A3 | K | −50 | −100 | — | +14 | +17 | −31% | +19% | +11% | 60 |
| A4 | T | −44 | 0 | −8 | +50 | +66 | +115% | −30% | −16% | n.a. |
| A5 | K | −26 | +64 | — | −38 | −300 | −72% | +39% | −8% | <37 |
| A6 | K | −28 | −27 | 0 | +13 | +33 | −100% | +8% | +6% | <37 |
| A7 | T | −9 | 0 | 0 | +11 | +17 | +1709% | −8% | +4% | 72 |
| A8 | T | −66 | −63 | −84 | +200 | +300 | +252% | +3% | −4% | <37 |
| A9 | T | −67 | −67 | −69 | +113 | +200 | +2056% | +7% | 0% | 123 |
| A10 | T | −47 | −62 | — | +7 | +25 | +2152% | −27% | 6% | <37 |

T = Product from example 1
K = Product from example 2
E = erythema, S = scaling, EX = exudation
SB = subjective improvement, J= improvement in itching

We claim:

1. A method for treating a skin disease in a patient, comprising administering intravenously to a patient suffering from a skin disease an effective amount of an emulsion comprising at least one polyunsaturated long-chain omega-3 or omega-6 fatty acid, or a pharmaceutically acceptable ester or salt thereof, and a conventional additive.

2. A method according to claim 1, wherein the fatty acid contains 18–22 carbon atoms.

3. A method according to claim 1, wherein
   (a) the omega-3 fatty acid is selected from α-linolenic acid, eicosapentaenoic acid (EPA) or docosahexaenoic acid (DCHA); and
   (b) the omega-6 fatty acid is selected from linolenic acid, γ-linolenic acid, dihomo-γ-linolenic acid or arachidonic acid.

4. A method according to claim 3, wherein the omega-3 fatty acid is eicosapentaenoic acid.

5. A method according to claim 1, wherein
   (a) the omega-3 fatty acid is present in a form selected from a fish oil, a highly purified fish oil concentrate or a linseed oil; and
   (b) the omega-6 fatty acid is present in a form selected from primrose oil, borage oil or soybean oil.

6. A method according to claim 1, wherein the ester is an ethyl ester or a glyceride ester.

7. A method according to claim 6, wherein the ester is a triglyceride.

8. A method according to claim 6, wherein the omega-3 or omega-6 fatty acid ester or salt is present in an amount of 4 to 45% by weight in the emulsion.

9. A method according to claim 8, wherein the omega-3 or omega-6 fatty acid, ester or salt is present in an amount of 10 to 30% by weight.

10. A method according to claim 8, wherein the emulsion further comprises phospholipids of vegetable or animal origin as emulsifiers.

11. A method according to claim 10, wherein said emulsifier is ovolecithin.

12. A method according to claim 10, wherein said emulsifier is present in an amount of 5 to 15% by weight based on the total fat content.

13. A method according to claim 1, wherein said emulsion is administered in combination with at least one added ingredient or therapy selected from the group consisting of a retinoid, a cignolin, phototherapy, balneophototherapy, a topical corticosteroid, a parenteral corticosteroid, an oral corticosteroid, a non-steroidal antiphlogistic and an antihistamine.

* * * * *